United States Patent [19]

Utts et al.

[11] Patent Number: 4,533,489
[45] Date of Patent: Aug. 6, 1985

[54] FORMABLE LIGHT REFLECTIVE COMPOSITIONS

[75] Inventors: Bradley K. Utts, Oakwood Village; Oley D. Wimer, Hudson, both of Ohio

[73] Assignee: Harshaw/Filtrol Partnership, Cleveland, Ohio

[21] Appl. No.: 559,150

[22] Filed: Dec. 7, 1983

[51] Int. Cl.³ ............................................. C09K 11/06
[52] U.S. Cl. ........................... 252/301.17; 250/458.1; 250/483.1; 250/487.1; 252/301.18
[58] Field of Search ...................... 252/301.17, 301.18; 250/458.1, 483.1, 487.1

[56] References Cited

U.S. PATENT DOCUMENTS 4,363,155 12/1982 Oi et al. .......................... 252/301.17
4,374,749 2/1983 Cusano et al. .................. 252/301.18

OTHER PUBLICATIONS

Bohm et al., Chem. Abstracts vol. 93, #115463.
Miyata, Chem. Abstracts vol. 94 #4807a.
Kirk-Othmer, Encyclopedia of Polymer Science & Technology; John Wiley; N.Y., N.Y., 1970, vol. 6, pp. 740-746, 758, vol. 12, pp. 534-536 and pp. 355-360, vol. 13 pp. 497-498.

*Primary Examiner*—Arthur P. Demers
*Attorney, Agent, or Firm*—James A. Lucas; Armand P. Boisselle

[57] ABSTRACT

A light-reflective, flowable and curable composition is described which comprises a resin containing light-reflective solid particles in an amount and of average particle size sufficient to provide the desired light reflectance/transmittance characteristics to the cured composition. Preferably, the composition is self-leveling, and the solid particles may be particles of magnesium oxide, barium sulfate, aluminum oxide or mixtures thereof. The compositions of the invention are useful as reflective coatings in various applications such as for radiation detector devices including scintillator crystals.

25 Claims, 1 Drawing Figure

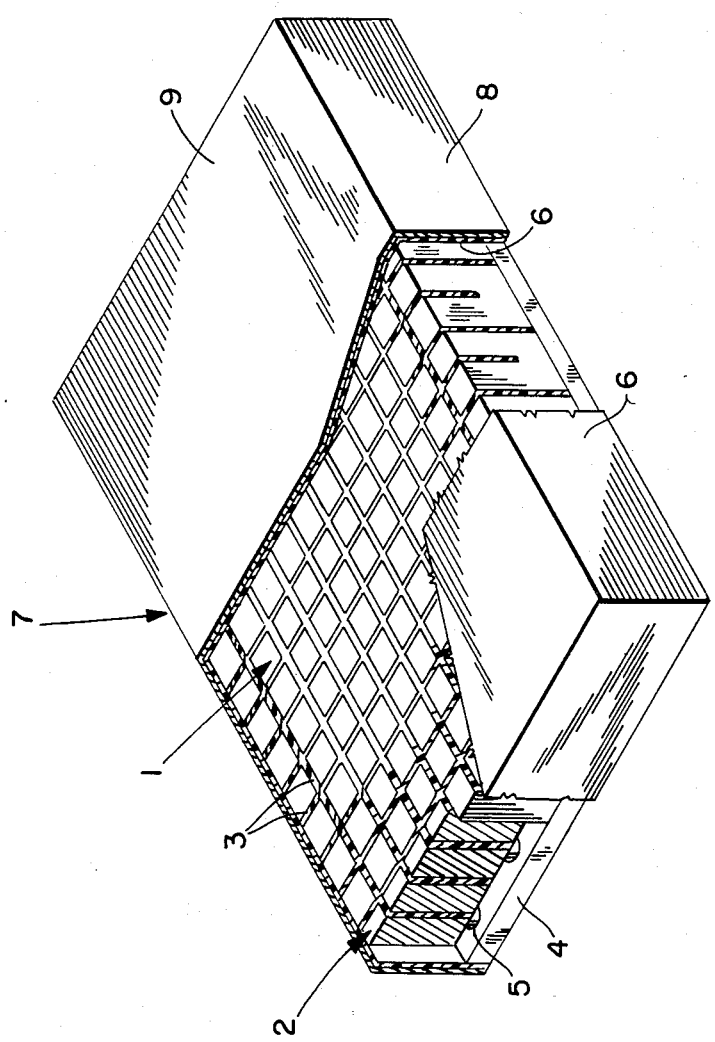

FORMABLE LIGHT REFLECTIVE COMPOSITIONS

BACKGROUND OF THE INVENTION

The present invention relates to light-reflective, curable compositions, and more particularly, to such compositions which comprise a resin containing light-reflective solid particles. Such compositions are useful as reflective coatings in various applications such as for scintillator crystals.

Radiation detectors have many applications and are particularly useful in the medical field in apparatus such as the gamma camera and X-ray (or gamma ray) image intensifiers. The radiation involved therein include gamma rays, X-rays and high energy nuclear particles such as electrons, protons, and neutrons.

One type of radiation detector utilized in such devices is based on scintillator crystals combined with photo-multiplier tubes. The scintillator crystal converts the invisible radiation to visible light. The light-sensitive photomultiplier tubes convert this light to an electric signal. A desirable objective when designing and utilizing scintillator crystals is to design the crystals so that the scintillator crystals will have maximum sensitivity to the incoming radiation, and the light photons will be concentrated and eventually pass out of the scintillator crystals at the highest possible intensity level.

SUMMARY OF THE INVENTION

The present invention relates to light-reflective, formable and curable compositions which can be utilized as reflective coatings on, for example, scintillator crystals to provide controlled reflectance/transmittance characteristics to the coated crystals. The light-reflective composition comprises a resin which contains light-reflective solid particles. The amount and average particle size distribution of the solid particles contained in the resin can be varied and controlled to provide the desired reflectance/transmittance characteristics. Preferably the curable compositions of the invention are capable of plastic flow, and more preferably the compositions are flowable and self-leveling under conditions of use.

BRIEF DESCRIPTION OF THE DRAWING

The drawing is a cut-away perspective view of a scintillator crystal orthogonal array detector having a coating of the light-reflective composition of the invention over the crystals.

DESCRIPTION OF THE PREFERRED EMBODIMENTS

The light-reflective, formable and curable compositions of the present invention comprise a resin containing light-reflective solid particles in an amount and of an average particle size distribution sufficient to provide the desired reflectance/transmittance characteristics to the cured composition. In applications where it is desired that the composition of the invention provide a coating which reflects substantially all of the light photons striking the composition, the composition should contain higher concentrations of the light-reflective solid particles. In general, such compositions may contain from about 1 to about 75 parts by weight of light-reflective solid particles per 100 parts by weight of resin. When it is desired to prepare a light-reflective cured composition characterized by a lower reflectance value, i.e., a greater transmittance value, lesser amounts of the solid particles can be utilized and such amounts may vary from about 1 to about 70% by weight of the light-reflective solid particles per 100 parts by weight of resin.

In conjunction with the amount of light-reflective solid particles included in the resin compositions, a second critical factor is the particle size or particle size distribution of the solid particles within the resin. It is generally believed that in order to provide maximum reflectance, the particle size distribution of the solid particles within the resin should be sufficient to provide substantially total resistance to the transmittance of any light photons through the cured resin composition. Optimally, to provide such high reflectance compositions, the amount and particle size distribution of the light reflective solid compounds within the resin should be sufficient to provide substantially particle-to-particle contact of the solid particles throughout the resin with any spaces between large particles being occupied by smaller particles of the same or different light-reflective material.

The relative amount of solid light-reflective particles included in the resin, and the particle size distribution of said particles to be used in any particular composition to provide compositions having the desired reflectance/transmittance characteristics can be determined readily by one skilled in the art. We generally have found that the reflectance/transmittance characteristics which we have desired could be achieved by utilizing light-reflective solid particles comprising a mixture of particles ranging in size from about 0.001 to about 20 microns and preferably from about 0.01 to about 5 microns.

A variety of resins may be utilized in the compositions of the invention provided that the mixture of resin and light-reflective solid particles prior to curing is formable. The term "resin" as used herein includes elastomers (rubbers) having the desired characteristics. Examples of resins which can be utilized include polyvinyl chlorides, polyurethanes, polyesters, polyamides, polyacrylates, butadienestyrene copolymers and natural rubber. Preferred resins are those which are flowable and self-leveling in the uncured state. The cured or set form of the light-reflective composition of the invention can range from soft, flexible rubber-like materials to hard solids depending upon the application. Particularly preferred resins are the room temperature curing silicone polymers. A variety of silicone rubber gum stocks are available commercially from the Dow Corning Corporation under the general trade names "Silastic" and "Sylgard". These resins are dimethyl polysiloxanes with vinyl, phenyl, methyl and trifluoropropyl groups attached thereto to modify the properties of the gums. Recommended curing agents for such silicones include peroxides such as benzoyl peroxide, dicumyl peroxide, and di-tert-butyl peroxide.

Room temperature vulcanizing silicone rubber compounds which are liquids or pastes that cure upon the addition of a curing agent to strong, durable, resilient rubber-like materials are available from the Silicon Products Department of General Electric under the general trade designation of "RTV Silicon Rubber". These silicone rubbers also are of the methyl phenyl type. Suitable curing agents include tin octoate, dibutyl tin dilaurate and lead octoate.

A variety of light-reflective solid particles and mixtures of one or more different solid materials can be utilized in the compositions of the invention, but the selection of particular solid particles generally will depend upon the intended end-use of the composition. For example, where the light-reflective compositions of the invention are to be used in environments which are sensitive to moisture, the non-hygroscopic solid particles should be selected for such applications. Examples of various light-reflective solid particles which can be utilized include magnesium oxide, barium sulfate, aluminum oxide, silicon oxide, etc., and mixtures thereof.

In some instances, in order to form compositions having reduced light reflectance, but little or no transmittance, the compositions of the invention also may contain light absorbing particles such as carbon particles mixed with the light-reflective particles. The amount of light absorbent particles contained in the resin may be as high as 10% by weight or more.

Particularly preferred light-reflective solid particles useful in the compositions of the invention are those of magnesium oxide, barium sulfate, aluminum oxide, and mixtures thereof. These materials can be prepared dry and are a highly light-reflective substances. As mentioned above, the particle size distribution of the particles incorporated into the compositions of the invention should be within the range of from about 0.001 to about 20 microns in diameter. Preferably, the particles utilized in preparing the compositions of the invention comprise a mixture of different size particles. In one embodiment, a useful mixture of aluminum oxide particles comprises a mixture (a) particles having an average particle size of about 3 microns and (b) particles having an average particle size of about 0.03 microns. More specifically, a useful mixture comprises from about 10 to 20 parts of the 3 micron particles and from about 1 to 10 parts of the 0.03 micron aluminum oxide particles per 100 parts of resin. As mentioned above, the selection of the particular particle sizes and amounts of the particles incorporated into the resin compositions can be varied depending upon the desired characteristics of the light-reflective composition which is formed.

The following examples illustrate the formulation and preparation of the light-reflective compositions of the invention. Unless otherwise indicated, all parts and percentages in the following examples, and in this entire specification, are by weight.

EXAMPLE 1

|  | Parts |
| --- | --- |
| RTV 655A, silicone resin from General Electric | 30 |
| RTV 655B, silicone catalyst General Electric | 3 |
| Aluminum oxide, 3 micron avg. | 15 |
| Aluminum oxide, 0.03 micron avg. | 5 |

The silicone resin is mixed thoroughly with the catalyst, and then the aluminum oxide powders are added with thorough mixing. The mixing is continued for a period of about 1 to 5 minutes until the totally paste-like mixture becomes wet. Air bubbles are removed by pumping down the mixture under vacuum. The composition then is maintained in a dry box. This composition is a flowable, self-leveling, light-reflective compound.

EXAMPLE 2

RTV 655A resin: 40 grams
RTV 655B, catalyst: 3 grams
Aluminum oxide, 3 micron avg.: 16 grams The mixing procedure described in Example 1 is utilized in this example. The product of this example is a flowable, self-leveling light-reflective composition.

EXAMPLE 3

RTV 655A resin: 40 grams
RTV 655B, catalyst: 3 grams
Aluminum oxide, 3 micron avg.: 12 grams The mixing procedure of Example 1 is repeated. The product of this example is a flowable, self-leveling, light-reflective composition.

EXAMPLE 4

RTV 670 resin: 40 grams
RTV 670 catalyst: 3 grams
Aluminum oxide, 3 micron avg.: 6 grams The light-reflective properties of the compositions of the invention as illustrated in the above examples can be determined in the following manner. A one-inch by one-inch sodium iodide crystal is placed in direct contact with a photomultiplier tube. The sides of the sodium iodide crystals not in contact with the photomultiplier tube are covered with aluminum. The sodium iodide crystal is subjected to gamma rays from a cesium 137 source. The sodium iodide crystal converts the gamma rays to light photons which are detected by the photomultiplier tube, and the intensity is observed through appropriate electronics in a display screen. The pulse height on the display screen is observed and recorded. In this controlled experiment, without the light-reflective compositions of the invention, the pulse height which is observed represents a transmission of 100%, or a light-reflectance of 0%.

The light-reflective/transmittance properties of the compositions of the invention are then measured by inserting a sample of the cured compositions of the invention of known thickness between the sodium iodide crystal and the photomultiplier tube. The above procedure, that is, subjecting the sodium iodide crystal to gamma rays from a cesium 137 source is repeated and the pulse height shown on the display screen is measured and recorded. The decrease in the pulse height which results from the placement of the compositions of the invention between the sodium iodide crystal and the photomultiplier tube is an indication of the amount of light which is not transmitted through the sample, but in fact reflected by the sample. The results obtained from several experiments utilizing the compositions obtained from Examples 1 through 4 are summarized in the following table. In the table, Samples 1-4 are samples of the cured compositions of Examples 1-4, respectively.

TABLE

| | Reflectance/Transmittance Properties | | | |
| --- | --- | --- | --- | --- |
| Sample | Thickness (inches) | Al$_2$O$_3$/Resin (wt. ratio) | Trans. (%) | Reduction (%)* |
| Control | — | — | 100% | — |
| 1 | 0.080 | 0.61 | 4.0 | 96 |
| 2 | 0.064 | 0.37 | 7.5 | 92.5 |
| 3 | 0.064 | 0.28 | 11.5 | 88.5 |

TABLE-continued

| | | Reflectance/Transmittance Properties | | |
|---|---|---|---|---|
| Sample | Thickness (inches) | Al$_2$O$_3$/Resin (wt. ratio) | Trans. (%) | Reduction (%)* |
| 4 | 0.064 | 0.19 | 26.7 | 73.3 |

*Measure of reflectance.

The light-reflective, formable and curable compositions of this invention are useful as reflective coatings for scintillator crystals such as sodium iodide, cesium fluoride, cesium iodide, barium fluoride, calcium fluoride, etc. The crystals may be doped with known dopants such as thallium, cesium, etc. The light-reflective compositions of the invention also are useful in treating other devices requiring optical reflectance where short cure times, controllability of light reflectance/transmittance and non-hygroscopicity are required or desired. As mentioned above, the compositions of the invention may be designed and prepared to provide compositions for use in applications where optical isolation, or controlled optical separation is required.

A particularly useful and beneficial application of the light-reflective, self-leveling flowable and curable composition of the invention is illustrated in the drawing which illustrates a cut-away view of a scintillator crystal block 1 mounted on a metal base 4 and contained within a light-reflective housing 7 having an aluminum top. Such an array could be used as a detector in a nuclear medicine imaging device. The device is useful, for example, to locate gamma radiation being emitted from a patient. In this embodiment, channels or grooves 3 have been made in scintillator crystal block by sawing the crystal in an orthogonal fashion, thereby resulting in the formation of multiple rectangular elements 2 separated from one another by channels 3. The various individual elements 2 within the crystal array can be optically isolated from one another through the use of the light-reflective compositions of the invention. Utilizing a composition of the present invention which is flowable and self-leveling, such as the compositions of Examples 1–4, the composition of the invention is poured onto the crystal array, and the composition forms a coating 6 on the elements and permeates into channels between the individual elements thereby filling the channels 3 and providing the desired optical isolation or controlled optical separation between the elements 2 as required. In the drawing, the light-reflective coating 6 is shown cut away even though in practice it covers all of the crystal elements.

In a device as illustrated in the FIGURE and described above, incoming gamma radiation causes a scintillation event in one of the elements of the matrix. By detecting the light emitted from the scintillation event, one may then determine which element of the matrix, and, therefore, the position at which the event occurred.

The coating 6 obtained from the compositions of the invention reflects the light produced in the individual elements of the array. The optical properties of the coating of such is to prevent light being transmitted from one element to another. This is desirable because the ability of the device to image accurately would be degraded if some of the light produced in the individual elements could be transmitted from one element to the other.

When the resin utilized in the preparation of the composition of the invention is a room-temperature curable resin such as General Electric's RTV 655A, the composition within the channels 3 can be cured easily at about room temperature in a short period of time up to 24 hours. At temperatures above room temperature, the curing of the composition is accelerated.

As illustrated in the drawing, the crystal 1 is mounted on a mask or light pipe containing circular openings 5 within permit the light emitted by the individual crystal elements 2 to pass downwardly, whereby such light can be detected by, for example, a photomultiplier tube (not shown). The entire crystal array is contained in closed housing 7 comprising base 4, sides 8 and top 9, which is aluminum or some other material transparent to gamma rays.

The preparation of the coated crystal array illustrated in the drawing is accomplished in the following manner when the crystal is a moisture sensitive crystal material such as a sodium iodide (thallium) crystal. The crystal is mounted on a mask and the base 4 (of the eventual closed housing 7) while keeping the crystal dry in a dry box. The crystal is then cut into rectangular elements 2 as illustrated using a saw while cooling the crystal with an anhydrous lubricant such as silicone oil. While still in the dry box, the crystal and base are placed in a tray and the sides 8 are added to base 4. The container formed by base 4 and sides 8 is filled with an anhydrous liquid such as silicone oil to a level sufficient to cover the crystal, and the crystal and container are transferred to another dry box where the crystals are coated with the composition of the invention as follows. A composition such as prepared in Example 1 is poured over the crystal. Since the composition is flowable and self-leveling, the composition flows over all the crystal sections 2 and into the channels 3 displacing the cooling oil and thoroughly filling the channels with composition. Any entrapped gas migrates to the surface thereby leaving a continuous film or coating substantially free of bubbles and imperfections. The composition then is cured by allowing the entire assembly to set for up to 24 hours at room temperature.

When the compositions of the invention are utilized in the manner illustrated in the drawing and described above, the scintillator crystal array which is obtained exhibits highly desirable levels of optical isolation between the individual crystal elements. When gamma rays penetrate the aluminum top 9 and the light reflective coating 6 which are both transparent to gamma rays, the gamma rays are converted to light photons within the crystal sections 2, and the only path said light photons can travel is downwardly through openings 5 in base 4 where the light can be detected and measured by photomultiplier tubes (not shown). Devices similar to that shown in the drawing have been studied to determine the amount of light that is transmitted from one section to another, and this transmittance has been found to be very low with a compound similar to the product of Example 1.

One significant result of the use of crystal arrays and the compositions of the invention as illustrated in the drawing is that large numbers of individual scintillator crystals can be replaced by a single smaller crystal which is partitioned and treated in accordance with the procedure described above. Consequently, the size of equipment utilizing multiple scintillator crystals can be significantly reduced, and equipment which has heretofore been large, cumbersome and non-portable can now be produced in a size which is significantly reduced thereby allowing the construction of equipment which is mobile and easily transported.

We claim:

1. A light-reflective, self-leveling flowable and curable composition comprising a silicone resin containing a mixture of aluminum oxide particles wherein the particles comprise a mixture of
   (a) particles having an average particle size of about 3 microns, and
   (b) particles having an average particle size of about 0.03 microns, said mixture of particles being present in an amount sufficient to provide the desired light-reflectance/transmittance characteristics to the cured composition.

2. The composition of claim 1 wherein the mixture comprises from about 10 to 20 parts of the particles having an average particle size of about 3 microns, and 1 to 10 parts of the particles having an average particle size of about 0.03 micron in 100 parts of resin.

3. The composition of claim 1 also containing up to 10% of carbon particles.

4. A scintillator crystal partially coated with a light-reflective, flowable and curable composition comprising a resin containing light-reflective solid particles in an amount and of an average particle size sufficient to provide the desired light-reflectance/transmittance characteristics to the cured composition.

5. The scintillator crystal of claim 4 wherein the composition is self-leveling.

6. The scintillator crystal of claim 4 wherein the resin is a silicone resin.

7. The scintillator crystal of claim 4 wherein the light-reflective solid particles are magnesium oxide, barium sulfate or aluminum oxide particles or mixtures thereof.

8. The scintillator crystal of claim 7 wherein the particles comprise a mixture of particles ranging in size from about 0.001 to about 20 microns in diameter.

9. The scintillator crystal of claim 4 containing from about 1 to about 75 parts by weight of light-reflective solid particles per 100 parts by weight of resin.

10. The scintillator crystal of claim 9 wherein the particles comprise a mixture of particles ranging in size from about 0.001 to about 20 microns.

11. A scintillator crystal partially coated with a light-reflective, self-leveling, flowable and curable composition comprising a silicone resin containing magnesium oxide, barium sulfate, or aluminum oxide particles or mixtures thereof having an average particle size of from about 0.01 to about 5 microns in diameter, said particles being present in an amount sufficient to provide the desired light-reflectance/transmittance characteristics to the cured composition.

12. The scintillator crystal of claim 11 wherein the particles are aluminum oxide particles comprising a mixture of (a) particles having an average particle size of about 3 microns and (b) particles having an average particle size of about 0.03 microns.

13. The scintillator crystal of claim 12 wherein the mixture comprises from about 10 to 20 parts of the 3 micron particles and 1 to 10 parts of the 0.03 micron particles in 100 parts of resin.

14. The scintillator crystal of claim 11 also containing up to 10% of carbon particles.

15. A plurality of scintillator crystal elements partially coated with a light-reflective, flowable and curable composition comprising a resin containing light-reflective solid particles in an amount and of an average particle size sufficient to provide the desired light-reflectance/transmittance characteristics to the cured composition and to provide optical isolation of one element from another.

16. The crystal elements of claim 15 wherein the composition is self-leveling.

17. The crystal elements of claim 15 wherein the resin is a silicone resin.

18. The crystal elements of claim 15 wherein the light-reflective solid particles are magnesium oxide, barium sulfate or aluminum oxide particles or mixtures thereof.

19. The crystal elements of claim 18 wherein the particles comprise a mixture of particles ranging in size from about 0.001 to about 20 microns in diameter.

20. The crystal elements of claim 15 containing from about 1 to about 75 parts by weight of light-reflective solid particles per 100 parts by weight of resin.

21. The crystal elements of claim 20 wherein the particles comprise a mixture of particles ranging in size from about 0.001 to about 20 microns.

22. The crystal element partially coated with a light-reflective, self-leveling, flowable and curable composition comprising a silicone resin containing magnesium oxide, barium sulfate, or aluminum oxide particles or mixtures thereof having an average particle size of from about 0.01 to about 5 microns in diameter, said particles being present in an amount sufficient to provide the desired light-reflectance/transmittance characteristics to the cured composition.

23. The crystal elements of claim 22 wherein the particles are aluminum oxide particles comprising a mixture of (a) particles having an average particle size of about 3 microns and (b) particles having an average particle size of about 0.03 microns.

24. The crystal elements of claim 23 wherein the mixture comprises from about 10 to 20 parts of the 3 micron particles and 1 to 10 parts of the 0.03 micron particles in 100 parts of resin.

25. The crystal elements of claim 23 wherein the composition also contains up to 10% of carbon particles.

* * * * *